US009457107B2

(12) United States Patent
Donnelly et al.

(10) Patent No.: US 9,457,107 B2
(45) Date of Patent: Oct. 4, 2016

(54) CAGE AMINE LIGANDS FOR METALLO-RADIOPHARMACEUTICALS

(71) Applicant: The University of Melbourne, Carlton (AU)

(72) Inventors: Paul Donnelly, Victoria (AU); Brett Paterson, Victoria (AU)

(73) Assignee: The University of Melbourne, Victoria (AU)

( * ) Notice: Subject to any disclaimer, the term of this patent is extended or adjusted under 35 U.S.C. 154(b) by 0 days.

(21) Appl. No.: 14/363,219

(22) PCT Filed: Dec. 6, 2012

(86) PCT No.: PCT/AU2012/001484
§ 371 (c)(1),
(2) Date: Jun. 5, 2014

(87) PCT Pub. No.: WO2013/082656
PCT Pub. Date: Jun. 13, 2013

(65) Prior Publication Data
US 2014/0323718 A1    Oct. 30, 2014

Related U.S. Application Data

(60) Provisional application No. 61/567,262, filed on Dec. 6, 2011.

(51) Int. Cl.
*A61K 51/04*  (2006.01)
*A61K 51/08*  (2006.01)
*C07D 487/08* (2006.01)

(52) U.S. Cl.
CPC ......... *A61K 51/0482* (2013.01); *A61K 51/088* (2013.01); *C07D 487/08* (2013.01)

(58) Field of Classification Search
CPC ........... A61K 51/0482; A61K 51/088; C07D 487/08
See application file for complete search history.

(56) References Cited

FOREIGN PATENT DOCUMENTS

| WO | WO-9531202 A1 | 11/1995 |
| WO | WO-03063912 A1 | 8/2003 |
| WO | WO-2005037862 A1 | 4/2005 |
| WO | WO-2010063069 A1 | 6/2010 |
| WO | WO-2010/121133 A2 | 10/2010 |

OTHER PUBLICATIONS

Bowman-James, K., Encyclopedia of Inorganic Chemistry, Macrocyclic Ligands (2006) John Wiley & Sons, Ltd. p. 1-20.*
Sultana, N. M., "Erythromycin synergism with essential and trace elements." Pakistan journal of pharmaceutical sciences 18.2 (2005): 35-39.*
"Macrocyclic, adj." OED Online. Oxford University Press, Sep. 2015. Web. Sep. 24, 2015, p. 1.*
"Synthon, n." OED Online. Oxford University Press, Sep. 2015. Web. Sep. 24, 2015, p. 1.*
Ma, M.T., "Gallium-68 complex of a macrobicyclic cage amine chelator tethered to two integrin-targeting peptides for diagnostic tumor imaging." Bioconjugate chemistry 22.10 (2011): 2093-2103.*
"International Application Serial No. PCT/AU2009/001572, International Preliminary Report on Patentability mailed Jun. 16, 2011", 8 pgs.
"International Application Serial No. PCT/AU2009/001572, International Search Report mailed Mar. 10, 2010", 3 pgs.
"International Application Serial No. PCT/AU2009/001572, Written Opinion mailed Mar. 10, 2010", 7 pgs.
Kramer, A, et al., "Derivatives of 1,3,5-triamino-1,3,5-trideoxy-cis-inositol as versatile pentadentate ligands for protein labeling with Re-186/188. prelabeling, biodistribution, and X-ray structural studies", Bioconjugate Chem., 9(6), (Nov. 1998), 691-702.
Lengkeek, N. A, "Functional Cage-Amine Complexes: Polymerisable Metallomonomers and Multi-Cage Complexes", PhD Thesis, University of Western Australia, (Dec. 2007), 254 pgs.
"File Registry on STN, RN 1334582-67-0", (2016), 1 page.
"Japanese Patent Application Serial No. 2014-545038, Office Action mailed Jul. 12, 2016", 37 pages.
Chen, Kai, et al., "Strain-Promoted Catalyst-Free Click Chemistry for Rapid Construction of $^{64}$Cu-Labeled PET Imaging Probes", ACS Med. Chem. Lett., 3(12), (2012), 1019-1023.
Huang, Chiun-Wei, et al., "Biological Stability Evaluation of the α2β1 Receptor Imaging Agents: Diamsar and DOTA Conjugated DGEA Peptide", Bioconjugate Chemistry, 22(2), (2011), 256-263.
Huang, Chiun-Wei, et al., "Design, synthesis and validation of integrin α2β1-targeted probe for microPET imaging of prostate cancer", European Journal of Nuclear Medicine and Molecular Imaging, 38(7), (2011), 1313-1322.
Ma, Michelle T, et al., "Macrobicyclic Cage Amine Ligands for Copper Radiopharmaceuticals: A Single Bivalent Cage Amine Containing Two Lys$^3$-bombesin Targeting Peptides", Inorganic Chemistry, 50, (2011), 6701-6710.

* cited by examiner

*Primary Examiner* — Samantha Shterengarts
*Assistant Examiner* — Matt Mauro
(74) *Attorney, Agent, or Firm* — Schwegman Lundberg & Woessner, P.A.

(57) ABSTRACT

The present invention relates to compounds that are useful as metal ligands and which can be bound to a biological entity such as a molecular recognition moiety and methods of making these compounds. Once the compounds that are bound to a biological entity are coordinated with a suitable metallic radionuclide, the coordinated compounds are useful as radiopharmaceuticals in the areas of radiotherapy and diagnostic imaging. The invention therefore also relates to methods of diagnosis and therapy utilizing the radiolabelled compounds of the invention.

16 Claims, No Drawings

CAGE AMINE LIGANDS FOR METALLO-RADIOPHARMACEUTICALS

PRIORITY APPLICATIONS

This application is a U.S. National Stage Filing under 35 U.S.C. 371 from International Application No. PCT/AU2012/001484, filed on 6 Dec. 2012, and published as WO 2013/082656 A1 on 13 Jun. 2013, which claims the benefit under 35 U.S.C. 119(e) to U.S. Provisional Application No. 61/567,262, filed on 6 Dec. 2011; which applications and publication are incorporated herein by reference in their entirety.

FIELD

The present invention relates to compounds that are useful as metal ligands and which can be bound to a biological entity such as a molecular recognition moiety and methods of making these compounds. Once the compounds that are bound to a biological entity are coordinated with a suitable metallic radionuclide, the coordinated compounds are useful as radiopharmaceuticals in the areas of radiotherapy and diagnostic imaging. The invention therefore also relates to methods of diagnosis and therapy utilising the radiolabelled compounds of the invention.

BACKGROUND

Radiolabelled compounds may be used as radiopharmaceuticals in a number of applications such as in radiotherapy or diagnostic imaging. In order for a radiolabelled compound to be employed as a radiopharmaceutical there are a number of desirable properties that the compound should ideally possess such as acceptable stability and, where possible, a degree of selectivity or targeting ability.

Initial work in the areas of radiopharmaceuticals focussed on simple metal ligands which were generally readily accessible and hence easy to produce. A difficulty with many of these radiolabelled compounds is that the complex formed between the ligand and the metal ion was not sufficiently strong and so dissociation of the metal ion from the ligand occurred in the physiological environment. This was undesirable as with the use of ligands of this type there was no ability to deliver the radiopharmaceutical to the desired target area in the body as metal exchange with metal ions in the physiological environment meant that when the radiopharmaceutical compound arrived at the desired site of action the level of radiolabelled metal ion coordinated to the compound had become significantly reduced. In addition where this type of exchange is observed the side effects experienced by the subject of the radiotherapy or radio-imaging are increased as radioactive material is delivered to otherwise healthy tissue in the body rather than predominantly to its place of action.

In order to overcome the problem of metal dissociation in the physiological environment a number of more complicated ligands have been developed and studied over time. Thus, for example a wide range of tetra-azamacrocycles based on the cyclam and cyclen framework have been investigated. Examples of ligands of this type include DOTA and TETA.

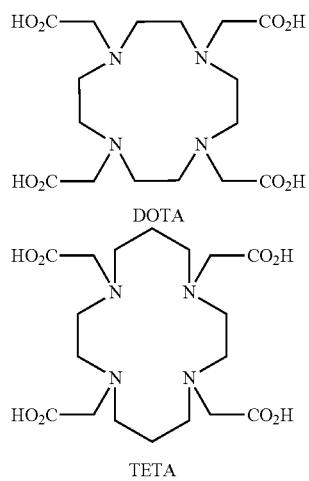

Unfortunately, even with these ligands there is still dissociation of the metal with certain derivatives. For example, some derivatives suffer from dissociation of Cu from the chelate as a consequence of transchelation to biological ligands such as copper transport proteins either as $Cu^{2+}$ or following in vivo reduction to $Cu^+$.

In order to increase the stability of radiolabelled compounds therefore hexaminemacrobicyclic cage amine ligands, known by their trivial name sarcophagines have been developed. These cage ligands form remarkably stable complexes with metals such as $Cu^{2+}$ and have fast complexation kinetics even at low concentrations of metal at ambient temperatures. These features therefore make ligands of this type particularly well suited in radiopharmaceutical applications, especially those applications involving copper.

Once the problem of stability of the complex between the ligand and the metal had been overcome attention turned to developing ways in which the ligand could be functionalised to incorporate targeting molecules within the ligand without compromising the stability of the metal ligand complex or the ultimate biological activity of the targeting molecule. A number of different targeting molecules are known in the art and the issue became how best to attach these to the ligand molecules.

In general the targeting molecule (or molecular recognition moiety as it is sometimes known) is attached to the ligand to provide a final compound containing both a ligand and a molecular recognition moiety. Whilst these compounds may contain a single molecular recognition moiety they may also be multimeric constructs where the ligand is attached to two (or more) molecular recognition moieties. This is typically desirable as a multimeric construct can possess higher affinity for a target receptor than its monomeric equivalent. This is in part due to an increase in the local concentration of the targeting group, allowing it to compete more effectively with endogenous ligands. In addition in circumstances where there is sufficient length between two or more targeting groups within a multimeric construct, then cooperative binding is possible, and two or more targeting groups will bind to two or more receptor sites at the same time. Indeed it has been observed that in vivo, a multimeric construct often demonstrates higher target tissue accumulation than its monomeric equivalent. Without wishing to be bound by theory it is thought that this is due to the higher affinity of the multimeric construct for the target receptor than that of the monomeric construct. Furthermore, the multimeric construct has a higher molecular weight than the monomeric construct and therefore prolonged bioavailability (as it is more resistant to degradation in the physiological environment). This can result in increased accumulation and retention in target tissue.

Initial work in the caged ligand area looked at direct coupling reactions of the primary amines of the cage amine 'diaminosarcophagine', 1,8-diamino-3,6,10,13,16,19-hexaaza bicyclo[6.6.6]icosane ($(NH_2)_2sar$), with peptides using standard coupling procedures. Unfortunately for a variety of reasons this has proven to be relatively inefficient and work in this area ceased. Workers then focussed on the incorporation of an aromatic amine to produce SarAr. The pendent aromatic amine can be used in conjugation reactions with the carboxylate residues of peptides or antibodies and it has been shown that SarAr could be conjugated to anti-GD2 monoclonal antibody (14.G2a) and its chimeric derivative (ch14.8) and the conjugate has been radiolabelled with $^{64}Cu$.

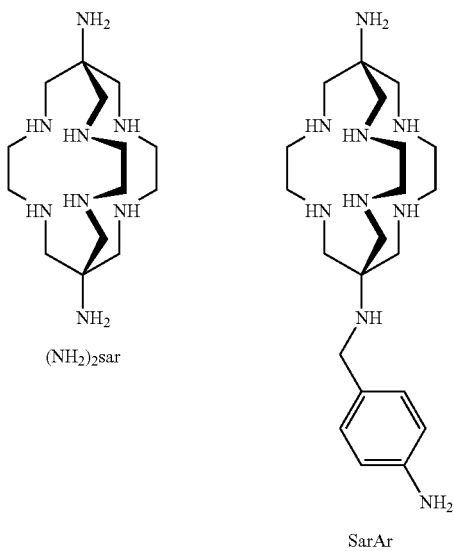

A difficulty with this approach is that in reaction of the aromatic amine in the conjugation step there are 8 other nitrogen atoms in the SarAr molecule that are available for competing reactions leading to the potential for the creation of a large number of impurities that is undesirable from a pharmaceutical sense. Whilst these could potentially be overcome by the use of substantial protective group chemistry this is clearly undesirable from a synthetic standpoint and scale up on a commercial scale.

An alternative approach has been to elaborate the ligand to incorporate carboxylate functional groups and incorporate peptides or antibodies via their N-terminal amine residues and this approach is of particular importance when the C-terminus is crucial to biological activity. Studies have shown that $(NH_2)_2sar$, can be functionalised with up to four carboxymethyl substituents via alkylation reactions with chloroacetic acid and the introduced carboxymethyl arms can be used as a point of further functionalisation and EDC-coupling reactions can then be used to introduce amino acids.

Unfortunately a potential disadvantage of these systems is that intramolecular cyclisation reactions can still occur in which the carboxymethyl arm reacts with a secondary amine of the cage framework to form lactam rings resulting in quadridentate rather than sexidentate ligands. Accordingly whilst this approach can be followed the potential for unwanted side reactions is clearly undesirable from a commercial perspective.

Further studies directed towards the functionalisation of ($(NH_2)_2sar$) was based around its reaction with activated di-carbonyl compounds such as acid anhydrides leading to the formation of an amide bond to the amine nitrogen and a free carboxylic acid moiety which was available for further elaboration to the desired binding onto a molecular recognition moiety. This lead to the formation of a carbonyl moiety as the "stick" end on the cage ligand and this was not always easy to elaborate by attachment to the molecular recognition moiety as was optimal. Accordingly there was a desire to probe ways in which the cage ligand with a pendant carboxylic acid moiety could be attached to a biological entity to make this step in the overall process more efficient.

SUMMARY

In one aspect there is provided a method of functionalising a compound of the formula (1) or a metal complex thereof:

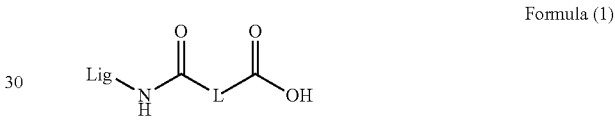

Formula (1)

wherein Lig is a nitrogen containing macrocyclic metal ligand;
$L$ is a bond or a linking moiety;
to modify its ability to bind to a biological entity the method comprising;
(a) converting the compound of formula (1) or a metal complex thereof to a compound of formula (2) or a metal complex thereof

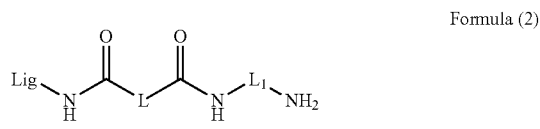

Formula (2)

wherein $L^1$ is a spacer group;
(b) converting the compound of formula (2) or a metal complex thereof to a compound of formula (3) or a metal complex thereof

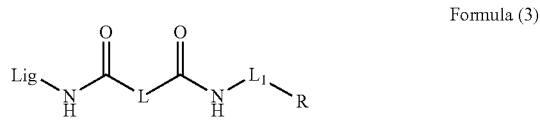

Formula (3)

wherein R is a moiety capable of binding to a biological entity or a protected form thereof or a synthon thereof.

In the steps of the present method the conversions or reactions may be carried out on the compounds per se or their metal complexes. Whilst the reactions can be carried out on the uncomplexed compounds in many instances this is undesirable as nitrogen atoms in the nitrogen containing macrocyclic metal ligand may interfere with the desired reaction. As such by first forming the metal complex the metal acts to de-activate these nitrogens in the nitrogen containing macrocyclic metal ligand and so acts as a pseudo protecting group for the ligand nitrogen atoms. As such in one embodiment it is desirable to carry out the conversions and reactions on the metal complex of the compound in question. A number of metals may be used for this purpose with magnesium being found to be particularly suitable.

By elaborating the compound of formula (1) above using the method outlined a large number of functionalised metal chelating ligands can be produced. Accordingly in an even further aspect the present invention provides a compound of the formula (3):

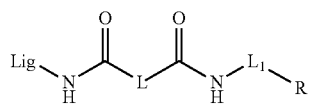

Formula (3)

wherein Lig is a nitrogen containing macrocyclic metal ligand;

L is a bond or a linking moiety;

$L^1$ is a spacer group;

R is a moiety capable of binding to a biological entity or a protected form thereof or a synthon thereof;

As with any group of structurally related compounds which possess a particular utility, and methods for their production, certain embodiments of variables of the compounds of the formula (3) which are particularly useful in their end use application.

In the compounds of formula (3) the L moiety serves as a linking moiety that serves to act as a spacer between the two carbonyl moieties which separate the ligand which can be bound to the radionuclide and the point of further elaboration. As such whilst it is desirable that there be a certain degree of separation between the two in order to ensure that the two entities do not interfere with each other's activity it is also important that the two are not so far removed such that the radionuclide is not effectively delivered to its site of operation.

In some embodiments L is a linking moiety having from 1 to 20 atoms in the normal chain. In some embodiments L is a linking moiety having from 1 to 15 atoms in the normal chain. In some embodiments L is a linking moiety having from 1 to 12 atoms in the normal chain. In some embodiments L is a linking moiety having from 1 to 10 atoms in the normal chain. In some embodiments L is a linking moiety having from 1 to 8 atoms in the normal chain. In some embodiments L has 8 atoms in the normal chain. In some embodiments L has 7 atoms in the normal chain. In some embodiments L has 6 atoms in the normal chain. In some embodiments L has 5 atoms in the normal chain. In some embodiments L has 4 atoms in the normal chain. In some embodiments L has 3 atoms in the normal chain. In some embodiments L has 2 atoms in the normal chain. In some embodiments L has 1 atom in the normal chain.

A wide range of possible moieties may be use to create a linking moiety of this type. Examples of suitable moieties that may be used in the creation of L include optionally substituted $C_1$-$C_{12}$alkyl, substituted $C_2$-$C_{12}$heteroalkyl, optionally substituted $C_3$-$C_{12}$cycloalkyl, optionally substituted $C_6$-$C_{18}$aryl, and optionally substituted $C_1$-$C_{18}$heteroaryl.

In some embodiments L is a group of the formula:

—(CH$_2$)$_q$CO(AA)$_r$NH(CH$_2$)$_s$— wherein each AA is independently an amino acid group;

q is an integer selected from the group consisting of 1, 2, 3, 4, 5, 6, 7, and 8;

r is an integer selected from the group consisting of 0, 1, 2, 3, 4, 5, 6, 7, and 8;

s is an integer selected from the group consisting of 0, 1, 2, 3, 4, 5, 6, 7, and 8.

In some embodiments q is 1. In some embodiments q is 2. In some embodiments q is 3. In some embodiments q is 4. In some embodiments q is 5. In some embodiments q is 6. In some embodiments q is 7. In some embodiments q is 8.

In some embodiments r is 0. In some embodiments r is 1. In some embodiments r is 2. In some embodiments r is 3. In some embodiments r is 4. In some embodiments r is 5. In some embodiments r is 6. In some embodiments r is 7. In some embodiments r is 8.

In some embodiments s is 0. In some embodiments s is 1. In some embodiments s is 2. In some embodiments s is 3. In some embodiments s is 4. In some embodiments s is 5. In some embodiments s is 6. In some embodiments s is 7. In some embodiments s is 8.

In some embodiments the amino acid is a naturally occurring amino acid. In some embodiments the amino acid is a non-naturally occurring amino acid. In some embodiments the amino acid is selected from the group consisting of phenyl alanine, tyrosine, amino hexanoic acid and cysteine.

In some embodiments q is 3, r is o and s is 5. In these embodiments X is a group of the formula:

—(CH$_2$)$_3$CONH(CH$_2$)$_5$—

In some embodiments L is a group of the formula:

—(CH$_2$)$_a$—, wherein optionally one or more of the CH$_2$ groups may be independently replaced by a heteroatomic group selected from S, O, P and NR$^4$ where R$^4$ is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl;

a is an integer selected from the group consisting of 1, 2, 3, 4, 5, 6, 7, 8, 9, 10, 11, 12, 13, 14 and 15.

In some forms of these embodiments the L group may contain a poly ethoxy group (PEG). In some embodiments L is a group of the formula:

—(CH$_2$)$_l$—(CH$_2$CH$_2$O)$_m$(CH$_2$)$_n$— wherein l is an integer selected from the group consisting of 0, 1, 2, 3, 4, 5, 6, 7, 8, 9, and 10;

wherein m is an integer selected from the group consisting of 0, 1, 2, 3, 4, 5, 6, 7, 8, 9, and 10; and wherein n is an integer selected from the group consisting of 0, 1, 2, 3, 4, 5, 6, 7, 8, 9, and 10.

In some embodiments l is selected from the group consisting of 0, 1, 2, 3, 4, and 5. In some embodiments l is 5. In some embodiments l is 4. In some embodiments l is 3. In some embodiments l is 2. In some embodiments l is 1. In some embodiments l is 0.

In some embodiments m is selected from the group consisting of 0, 1, 2, 3, 4, and 5. In some embodiments m is 5. In some embodiments m is 4. In some embodiments m is 3. In some embodiments m is 2. In some embodiments m is 1. In some embodiments m is 0.

In some embodiments n is selected from the group consisting of 0, 1, 2, 3, 4, and 5. In some embodiments n is 5. In some embodiments n is 4. In some embodiments n is 3. In some embodiments m is 2. In some embodiments n is 1. In some embodiments n is 0.

Specific examples of L groups of this type include —CH$_2$—(CH$_2$CH$_2$O)$_3$(CH$_2$)$_3$—; and —(CH$_2$CH$_2$O)$_3$(CH$_2$)$_2$—. As will be appreciated by a skilled worker in the field the values of l, m and n can be varied widely to arrive at a large number of possible L groups of this type.

In some embodiments L is a group of the formula:

wherein optionally one or more of the $CH_2$ groups may be independently replaced by a heteroatomic group selected from S, O, P and $NR^4$ where $R^4$ is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl; and a is an integer selected from the group consisting of 1, 2, 3, 4, 5, 6, 7, 8, 9 and 10.

In some embodiments a is selected from the group consisting of 1, 2, 3, 4, and 5. In some embodiments a is 4. In some embodiments a is 3. In some embodiments a is 2. In some embodiments a is 1.

In some embodiments L is selected from the group consisting of —$CH_2$—, —$CH_2CH_2$—, —$CH_2CH_2CH_2$—, —$CH_2CH_2CH_2CH_2$— and —$CH_2OCH_2$—.

In some embodiments L is —$(CH_2)$—. In some embodiments L is —$(CH_2)_2$—. In some embodiments L is —$(CH_2)_3$—. In some embodiments L is —$(CH_2)_4$—. In some embodiments L is —$(CH_2)_5$—. In some embodiments L is —$(CH_2)_6$—. In some embodiments L is —$(CH_2)_7$—. In some embodiments L is —$(CH_2)_8$—. In some embodiments L is —$(CH_2)_9$—. In some embodiments L is —$(CH_2)_{10}$—.

In some embodiments the ligand (Lig) may be a tetra-azamacrocycle based on the cyclam and cyclen framework. In some embodiments Lig is a nitrogen containing cage metal ligand. Cage ligands of this type are typically useful as they bind strongly to metal ions leading to a stable complex being formed.

In some embodiments Lig is a nitrogen containing cage metal ligand of the formula:

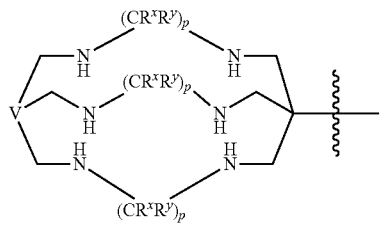

V is selected from the group consisting of N and $CR^1$;

each $R^x$ and $R^y$ are independently selected from the group consisting of H, $CH_3$, $CO_2H$, $NO_2$, $CH_2OH$, $H_2PO_4$, $HSO_3$, CN, $CONH_2$ and CHO;

each p is independently an integer selected from the group consisting of 2, 3, and 4;

$R^1$ is selected from the group consisting of H, OH, halogen, $NO_2$, $NH_2$, optionally substituted $C_1$-$C_{12}$alkyl, optionally substituted $C_6$-$C_{18}$aryl, cyano, $CO_2R^2$, $NHR^3$, $N(R^3)_2$ and a group of the formula:

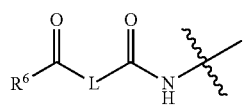

L is as defined above;

$R^6$ is selected from the group consisting of H, OH, $NH_2$, $NHR^3$, $N(R^3)_2$ and NH-$L^1$-R, $L^1$ is as defined above;

R is a moiety capable of binding to a biological entity or a protected form thereof or a synthon thereof;

$R^2$ is selected from the group consisting of H, halogen, an oxygen protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;

each $R^3$ is independently selected from the group consisting of H, L-R', a nitrogen protecting group, optionally substituted $C_1$-$C_{12}$alkyl, —(C=O)-substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl.

wherein L is as defined above;

R' is H, optionally substituted $C_1$-$C_{12}$alkyl, or a moiety capable of binding to a biological entity.

In some embodiments Lig is a nitrogen containing cage metal ligand of the formula:

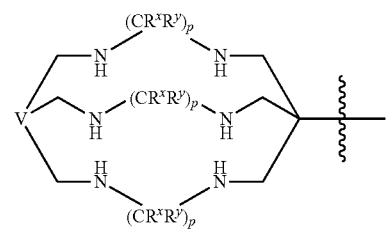

V is selected from the group consisting of N and $CR^1$;

each $R^x$ and $R^y$ are independently selected from the group consisting of H, $CH_3$, $CO_2H$, $NO_2$, $CH_2OH$, $H_2PO_4$, $HSO_3$, CN, $CONH_2$ and CHO;

each p is independently an integer selected from the group consisting of 2, 3, and 4;

$R^1$ is selected from the group consisting of H, OH, halogen, $NO_2$, $NH_2$, optionally substituted $C_1$-$C_{12}$alkyl, optionally substituted $C_6$-$C_{18}$aryl, cyano, $CO_2R^2$, $NHR^3$, $N(R^3)_2$, $R^2$ is selected from the group consisting of H, halogen, an oxygen protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;

each $R^3$ is independently selected from the group consisting of H, L-R', a nitrogen protecting group, optionally substituted $C_1$-$C_{12}$alkyl, —(C=O)-substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;

wherein L is as defined above and R' is H, optionally substituted $C_1$-$C_{12}$alkyl, or a moiety capable of binding to a biological entity.

In some embodiments Lig is a macrocyclic metal ligand of the formula:

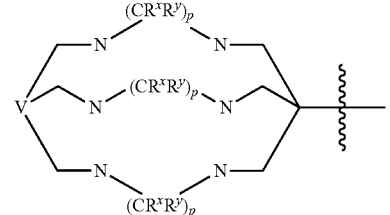

wherein $R^x$, $R^y$ and p are as defined above.

In some embodiments Lig is a macrocyclic ligand of the formula:

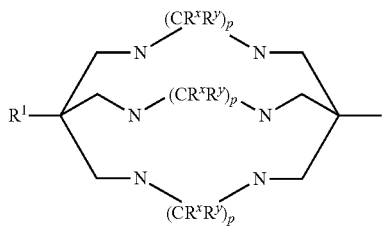

wherein $R^x$, $R^y$, $R^1$ and p are as defined above.

In some embodiments Lig is selected from the group consisting of:

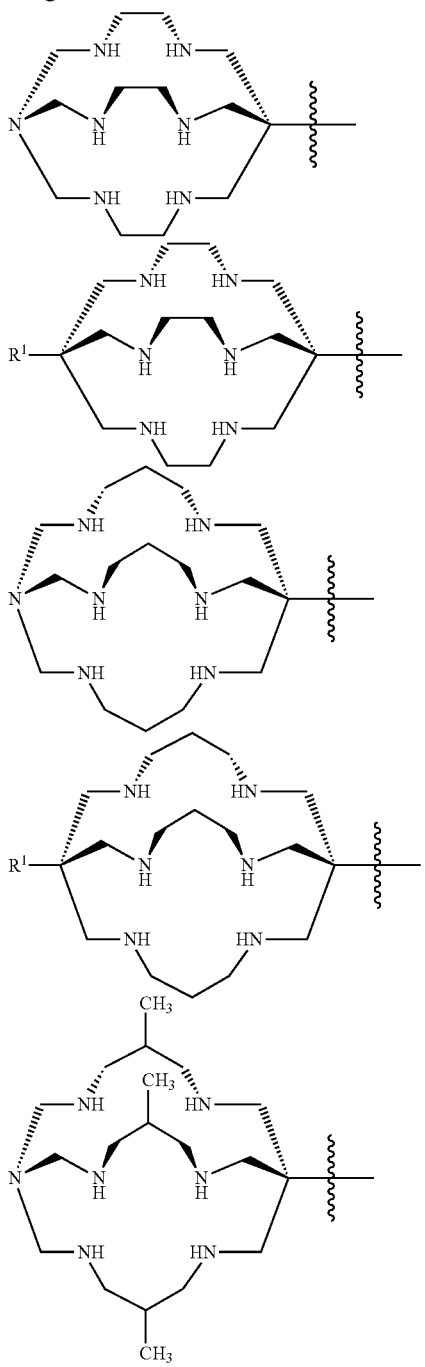

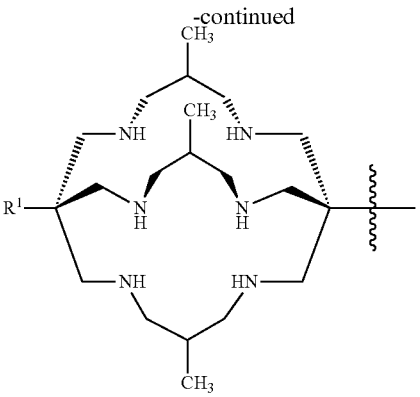

wherein $R^1$ is as defined above.

In some embodiments Lig is a group of the formula:

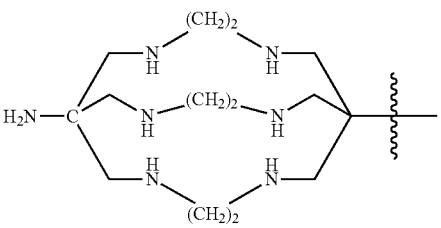

In some embodiments $L^1$ is a linking moiety having from 1 to 20 atoms in the normal chain.

In some embodiments $L^1$ is a group of the formula $$-(CH_2)_a-,$$

wherein optionally one or more of the $CH_2$ groups may be independently replaced by a heteroatomic group selected from S, O, P and $NR^4$ where $R^4$ is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl;

a is an integer selected from the group consisting of 1, 2, 3, 4, 5, 6, 7, 8, 9 and 10.

In some embodiments a is selected from the group consisting of 1, 2, 3, 4, and 5. In some embodiments a is 4. In some embodiments a is 3. In some embodiments a is 2. In some embodiments a is 1.

In some embodiments $L^1$ is selected from the group consisting of —$CH_2$—, —$CH_2CH_{2-3}$—$CH_2CH_2CH_{2-3}$ and —$CH_2CH_2CH_2CH_2$. In some embodiments $L^1$ is —$CH_2CH_2CH_2$—.

R is a moiety capable of binding to a biological entity, or a protected form thereof or a synthon thereof. The moiety may have the ability to bind to a biological moiety such as an antibody, a protein, a peptide, a carbohydrate, a nucleic acid, an oligonucleotide, an oligosaccharide and a liposome or a fragment or derivative thereof.

As such the R group reacts or binds to a complementary moiety on the biological entity of interest. For example in one embodiment the R moiety is a moiety capable of taking part in a click chemistry reaction with a complementary moiety on a biological entity. Examples of complementary paired functional groups that are well known to undergo "click" chemistry reactions are alkyne-azide, alkyne-nitrile oxide, nitrile-azide and maleimide-anthracene. Each of the paired complementary functional groups gives rise to cyclic moieties when they directly react with one another in a covalent cycloaddition reaction. The person skilled in the art would be able to select other functional group pairings capable of participating in cycloaddition reactions of this type that satisfy the requirements of click chemistry. In general thereof the identity of the R group will be chosen based on the relevant complementary R group on the biological entity of interest.

The R group may also react or bind to the biological entity by reaction with a pendant moiety on the biological entity (either naturally present or by modification of the biological entity). Once again a skilled worked in the field will be able to review the biological entity of interest in any specific circumstance and determine a suitable R group to bind to the pendant moieties on the R group.

In some embodiments R is selected from the group consisting of —NCS, $CO_2H$, $NH_2$, an azide, an alkyne, an isonitrile, a tetrazine, maleimide, or a protected form thereof or a synthon thereof.

In some embodiments of the compounds of the invention the nitrogen containing macrocyclic metal ligand is complexed with a metal ion. The ligand may be complexed with any suitable metal ion and may be used to deliver a range of metal ions. In some embodiments the metal in the metal ion is selected from the group consisting of Cu, Tc, Gd, Ga, In, Co, Re, Fe, Mg, Ca, Au, Ag, Rh, Pt, Bi, Cr, W, Ni, V, Ir, Pt, Zn, Cd, Mn, Ru, Pd, Hg, and Ti.

In some embodiments the metal in the metal ion is a radionuclide selected from the group consisting of Cu, Tc, Ga, Co, In, Fe, and Ti. The present compounds have been found to be particularly applicable useful in binding copper ions. In some embodiments the metal in the metal ion is a radionuclide selected from the group consisting of $^{60}Cu$, $^{62}Cu$, $^{64}Cu$ and $^{67}Cu$. In some embodiments the metal in the metal ion is $^{60}Cu$. In some embodiments the metal in the metal ion is $^{62}Cu$. In some embodiments the metal in the metal ion is $^{64}Cu$. In some embodiments the metal in the metal ion is $^{67}Cu$.

The invention also relates to pharmaceutical compositions including a compound of the invention as described above and a pharmaceutically acceptable carrier, diluent or excipient.

In one embodiment of the methods of the invention step (a) comprises the steps of:
(a1)) converting the compound of formula (1) or a metal complex thereof into a compound of formula (Ia) or a metal complex thereof:

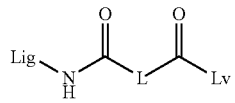

Formula (1a)

wherein Lv is a group that can be displaced by a nitrogen moiety in a nucleophillic substitution reaction;
(a2) reacting the compound of formula (1a) or a metal complex thereof with a nitrogen nucleophile of the formula:

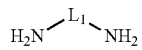

to form a compound of formula (2) or a metal complex thereof.

In some embodiments of the method the group Lv is a leaving group. In some embodiments steps (1a) and (1b) are carried out on the metal complexes of the respective compounds being reacted as the metal acts as a protecting group for the nitrogen atoms in the cage ligand.

In some embodiments the compound of formula (2) is converted to a compound of formula (3) by reacting the amine with a reagent selected from the group consisting of an azide, thiosphosgene, carbon disulphide and an acid anhydride. In some embodiments this reaction is carried out on the metal complex of the compound of formula (2). In some embodiments this reaction is carried out on the non-complexed or free compound of formula (2). In embodiments where this occurs in which the compound of formula (2) is produced as a metal complex the method includes an additional step of removing the metal complex prior to further reaction.

In some embodiments the reagent is an azide. In some embodiments the reagent is thiosphosgene. In some embodiments the reagent is carbon disulphide. In some embodiments the reagent is maleic anhydride.

These and other features of the present teachings are set forth herein.

DETAILED DESCRIPTION

In this specification a number of terms are used which are well known to a skilled addressee. Nevertheless for the purposes of clarity a number of terms will be defined.

As used herein, the term "unsubstituted" means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)R$^a$, —C(=O)OR$^a$, C(=O)NR$^a$R$^b$, C(=NOH)R$^a$, C(=NR$^a$)NR$^b$R$^c$, NR$^a$R$^b$, NR$^a$C(=O)R$^b$, NR$^a$C(=O)OR$^b$, NR$^a$C(=O)NR$^b$R$^c$, NR$^a$C(=NR$^b$)NR$^c$R$^d$, NR$^a$SO$_2$R$^b$, —SR$^a$, SO$_2$NR$^a$R$^b$, —OR$^a$, OC(=O)NR$^a$R$^b$, OC(=O)R$^a$ and acyl, wherein R$^a$, R$^b$, R$^c$ and R$^d$ are each independently selected from the group consisting of H, $C_1$-$C_{12}$alkyl, $C_1$-$C_{12}$haloalkyl, $C_2$-$C_{12}$alkenyl, $C_2$-$C_{12}$alkynyl, $C_2$-$C_{12}$heteroalkyl, $C_3$-$C_{12}$cycloalkyl, $C_3$-$C_{12}$cycloalkenyl, $C_2$-$C_{12}$heterocycloalkyl, $C_2$-$C_{12}$heterocycloalkenyl, $C_6$-$C_{18}$aryl, $C_1$-$C_{18}$heteroaryl, and acyl, or any two or more of $R^a$, $R^b$, $R^c$ and $R^d$, when taken together with the atoms to which they are attached form a heterocyclic ring system with 3 to 12 ring atoms.

In some embodiments each optional substituent is independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, —COOH, —SH, and acyl.

Examples of particularly suitable optional substituents include F, Cl, Br, I, CH$_3$, CH$_2$CH$_3$, OH, OCH$_3$, CF$_3$, OCF$_3$, NO$_2$, NH$_2$, and CN.

As used herein the term "amino acid" refers to a molecule which contains both an amine and a carboxyl function. The amino acid may be a natural or an unnatural amino acid.

"Alkenyl" as a group or part of a group denotes an aliphatic hydrocarbon group containing at least one carbon-carbon double bond and which may be straight or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkyl" as a group or part of a group refers to a straight or branched aliphatic hydrocarbon group, preferably a $C_1$-$C_{12}$alkyl, more preferably a $C_1$-$C_{10}$alkyl, most preferably $C_1$-$C_6$ unless otherwise noted. Examples of suitable straight and branched $C_1$-$C_6$alkyl substituents include methyl, ethyl, n-propyl, 2-propyl, n-butyl, sec-butyl, t-butyl, hexyl, and the like. The group may be a terminal group or a bridging group.

"Alkynyl" as a group or part of a group means an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$cycloalkyl or $C_{5-7}$cycloalkenyl group are fused together to form a cyclic structure, such as tetrahydronaphthyl, indenyl or indanyl. The group may be a terminal group or a bridging group. Typically an aryl group is a $C_6$-$C_{18}$aryl group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_9$cycloalkyl group. The group may be a terminal group or a bridging group.

"Halogen" represents chlorine, fluorine, bromine or iodine.

"Heteroalkyl" refers to a straight- or branched-chain alkyl group preferably having from 2 to 12 carbons, more preferably 2 to 6 carbons in the chain, in which one or more of the carbon atoms (and any associated hydrogen atoms) are each independently replaced by a heteroatomic group selected from S, O, P and NR' where R' is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl. Exemplary heteroalkyls include alkyl ethers, secondary and tertiary alkyl amines, amides, alkyl sulfides, and the like. Examples of heteroalkyl also include hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. A heteroaryl group is typically a $C_1$-$C_{18}$heteroaryl group. The group may be a terminal group or a bridging group.

A "leaving group" is a chemical group that is readily displaced by a desired incoming chemical moiety. Accordingly in any situation the choice of leaving group will depend upon the ability of the particular group to be displaced by the incoming chemical moiety. Suitable leaving groups are well known in the art, see for example "Advanced Organic Chemistry" Jerry March 4$^{th}$ Edn. pp 351-357, Oak Wick and Sons NY (1997). Examples of suitable leaving groups include, but are not limited to, halogen, alkoxy (such as ethoxy, methoxy), sulphonyloxy, optionally substituted arylsulfonyl. Specific examples include chloro, iodo, bromo, fluoro, ethoxy, methoxy, methansulphonyl, triflate and the like.

The term "normal chain" refers to the direct chain joining the two ends of a linking moiety.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state. An effective amount for radioimaging is typically sufficient to identify the radionuclide in the subject.

The term "molecular recognition moiety" refers to an entity capable of binding to a particular molecular entity, typically a receptor location in the physiological environment. The term includes antibodies, proteins, peptides, carbohydrates, nucleic acids, oligonucleotides, oligosaccharides and liposomes.

The term "oxygen protecting group" means a group that can prevent the oxygen moiety reacting during further derivatisation of the protected compound and which can be readily removed when desired. In one embodiment the protecting group is removable in the physiological state by natural metabolic processes. Examples of oxygen protecting groups include acyl groups (such as acetyl), ethers (such as methoxy methyl ether (MOM), β-methoxy ethoxy methyl ether (MEM), p-methoxy benzyl ether (PMB), methylthio methyl ether, Pivaloyl (Piv), Tetrahydropyran (THP)), and silyl ethers (such as Trimethylsilyl (TMS) tert-butyl dimethyl silyl (TBDMS) and triisopropylsilyl (TIPS).

The term "nitrogen protecting group" means a group that can prevent the nitrogen moiety reacting during further derivatisation of the protected compound and which can be readily removed when desired. In one embodiment the protecting group is removable in the physiological state by natural metabolic processes and in essence the protected compound is acting as a prodrug for the active unprotected species. Examples of suitable nitrogen protecting groups that may be used include formyl, trityl, phthalimido, acetyl, trichloroacetyl, chloroacetyl, bromoacetyl, iodoacetyl; urethane-type blocking groups such as benzyloxycarbonyl ('CBz'), 4-phenylbenzyloxycarbonyl, 2-methyl benzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl ('tBoc'), 2-(4-xenyl)-isopropoxycarbonyl, 1,1-diphenyleth-1-yloxycarbonyl, 1,1-diphenylprop-1-yloxycarbonyl, 2-phenylprop-2-yloxycarbonyl, 2-(p-toluoyl)-prop-2-yloxy-carbonyl, cyclo-pentanyloxy-carbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluoylsulfono)-ethoxycarbonyl, 2-(methylsulfono) ethoxycarbonyl, 2-(triphenylphosphino)-ethoxycarbonyl, fluorenylmethoxycarbonyl ("FMOC"), 2-(trimethylsilyl) ethoxycarbonyl, allyloxycarbonyl, 1-(trimethylsilylmethyl) prop-1-enyloxycarbonyl, 5-benzisoxalymethoxy carbonyl, 4-acetoxybenzyloxycarbonyl, 2,2,2-trichloroethoxycarbonyl, 2-ethynyl-2-propoxycarbonyl, cyclopropylmethoxycarbonyl, 4-(decycloxy)benzyloxycarbonyl, isobornyloxycarbonyl, 1-piperidyloxycarbonlyl and the like; benzoylmethylsulfono group, 2-nitrophenylsulfenyl, diphenylphosphine oxide, and the like. The actual nitrogen protecting group employed is not critical so long as the derivatised nitrogen group is stable to the condition of subsequent reaction(s) and can be selectively removed as required without substantially disrupting the remainder of the molecule including any other nitrogen protecting group(s). Further examples of these groups are found in: Greene, T. W. and Wuts, P. G. M., Protective Groups in Organic Synthesis, Second edition; Wiley-Interscience: 1991; Chapter 7; McOmie, J. F. W. (ed.), Protective Groups in Organic Chemistry, Plenum Press, 1973; and Kocienski, P. J., Protecting Groups, Second Edition, Theime Medical Pub., 2000.

The term 'click chemistry' is used to describe covalent reactions with high reaction yields that can be performed under extremely mild conditions. A number of 'click' reactions involve a cycloaddition reaction between appropriate functional groups to generate a stable cyclic structure. The most well documented click reaction is the Cu(I) catalyzed variant of the Huisgen 1,3-dipolar cycloaddition of azides and alkynes to form 1,2,3-triazoles. Many click reactions are thermodynamically driven, leading to fast reaction times, high product yields and high selectivity in the reaction.

The compounds of the invention as discussed above may include a wide variety of nitrogen containing macrocyclic metal ligands.

The ligand may be a monocyclic nitrogen containing metal ligand based on the cyclam or cyclen frameworks. Ligand of this type and derivatives thereof may be synthesised using methodology available in the art such as in Bernhardt (J. Chem. Soc., Dalton Transactions, 1996, pages 4319-4324), Bernhardt et al (J. Chem. Soc., Dalton Transactions, 1996, pages 4325-4330), and Bernhardt and Sharpe (Inorg Chem, 2000, 39, pages 2020-2025). Various other ligands of this general type may be made by variation of the procedures described in these articles.

The ligand may also be a cage like cryptand ligand as described for example in Geue (Chemical communications, 1994, page 667). Cryptand ligands of this type are described in U.S. Pat. No. 4,497,737 in the name of Sargeson et al, the disclosure of which is incorporated herein by reference.

The synthesis involves a metal ion template reaction and involves condensation of a tris-(diamine) metal ion complex (see column 3 lines 30 to 35) with formaldehyde and an appropriate nucleophile in the presence of base. The identity of the nucleophile will determine the identity of the substituents on the cage ligand and a skilled addressee can access a wide variety of substitution patterns around the cage ligand by judicious choice of the appropriate amine used in the condensation as well as the identity of the nucleophile.

In order to produce the compounds of formula (1) which are the staring material for the present invention the amino substituted ligand or a metal complexed form thereof is reacted with an appropriate dicarbonyl compound under suitable reaction conditions to arrive at the final product.

Whilst the reaction may be performed on the free ligand there is still a possibility of the reaction being compromised by the presence of the ring nitrogen(s). As such it is desirable to perform the reaction using a metal complex thereof as the metal serves to act as a protecting group for the secondary nitrogen atoms in the ring. Whilst this can be conducted using a number of different metals it is found that magnesium is particularly suitable.

The reaction may be carried out in any suitable solvent which is inert to the two reactants with the identity of the solvent being determined by the relative solubilities of the anhydride and the amine substituted metal ligand. Examples of solvents that may be used include aliphatic, aromatic, or halogenated hydrocarbons such as benzene, toluene, xylenes; chlorobenzene, chloroform, methylene chloride, ethylene chloride; ethers and ethereal compounds such as dialkyl ether, ethylene glycol mono or -dialkyl ether, THF, dioxane; nitriles such as acetonitrile or 2-methoxypropionitrile; N,N-dialkylated amides such as dimethylformamide; and dimethyl acetamide, dimethylsulphoxide, tetramethylurea; as well as mixtures of these solvents with each other.

The reaction may be carried out at any of a number of suitable temperatures with the reaction temperature being able to be readily determined on a case by case basis. Nevertheless the reaction temperature is typically carried out at from 0 to 100° C., more typically 50 to 80° C.

The reaction may be carried out using a wide variety of activated dicarbonyl compounds. In some embodiments the activated dicarbonyl compound is an anhydride of the formula:

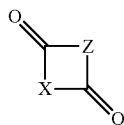

wherein L is as defined above and Z is O, S or NR$^2$.

Anhydride compounds of this type are generally readily available for certain values of L and thus these compounds may be readily used for values of L for which they are obtainable. It is desirable that they be utilised where possible as the potential for side reactions is reduced somewhat with these compounds.

In some embodiments the activated dicarbonyl compound is a compound of the formula:

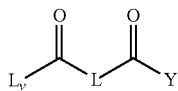

wherein L is as defined above. Y is OH or a protected from thereof and L$_v$ is a leaving group. The L$_v$ group on the compounds of this type may be any suitable leaving group but is typically selected from the group consisting of Cl, Br, CH$_3$SO$_3$, CH$_3$C$_6$H$_4$SO$_3$, and a group of the formula:

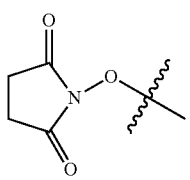 [SMILES: *ON1C(=O)CCC1=O]

In choosing a suitable leaving group for reactions of this type the skilled worker in the art will have regard for the functionality of the remainder of the molecule and the ease of production of the activated dicarbonyl compound in each instance.

The reaction is also typically carried out in the presence of a base as this is found to facilitate the reaction. Examples of suitable bases include hindered tertiary amines with trialkyl amines such as trimethylamine, triethyleneamine, diisopropylethyl amine being suitable examples of bases for use in the reaction. The amount of base used is such that it is in a significant molar excess so as to ensure that the reaction does not become affected by acidification as it progresses.

The exact compound produced will depend upon the reaction stoichiometry and the starting materials with a skilled addressee being able to adjust either of these variables to produce the desired final product.

In addition it is desired that the linker L be extended to be significantly longer than the compounds readily accessible by the route detailed above it is possible to elaborate the carboxy group (such as by standard peptide chemistry techniques) to introduce further amino acid groups to the chain. The methods of achieving reactions of this type are well within the skill of a skilled addressee in the area.

In the method of the invention the compounds of formula (1) are converted to compounds of formula (2). This conversion may be carried out in any way known in the art and may be carried out as a single step process or as a multi-step process.

In addition depending upon the substituents on the Lig group of the compounds of formula (1) it may be necessary to protect the substituents from interfering with the reaction. For example the applicants have found that where the Lig group contains a free amino group (such as will be the case if the original ligand was 1,8-diamino-Sar) and then it is desirable to first protect the amino group prior to reaction with a suitable nitrogen protecting group. An example of a suitable protecting group of this type is the acetyl group.

As stated previously the conversion may be a one step or a multi-step process. Thus for example an amide formation reaction could be carried out (typically in the presence of a coupling reagent) to form an amide bond by reaction of compound of formula (1) with a compound of the formula NH$_2$L$_1$NH$_2$. It has been found, however, that in many instances it is desirable to carry out the conversion as a multi-step process by first converting the carboxylic acid moiety to an activated form thereof.

Accordingly in some embodiments step (a) comprises the steps of:

(a1) converting the compound of formula (1) into a compound of formula (Ia)

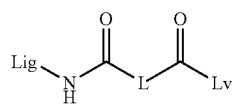

wherein Lv is a group that can be displaced by a nitrogen moiety in a nucleophillic substitution reaction;

(a2) reacting the compound of formula (1a) with a nitrogen nucleophile of the formula:

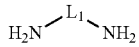

to form a compound of formula (2).

There are a number of ways in which the compound of formula (1) may be converted into a compound of formula (1a) to form a compound where the carboxylic acid moiety has been activated for further reaction with a nucleophillic species. Thus for example one well known way of activating carboxylic acids is to convert them to the corresponding acid chloride by reaction with thionyl chloride for example. In effect this transformation replaces the OH group (which is a relatively poor leaving group) with the Cl group which is a relatively good leaving group. A number of transformations of this type are known where the ability of the OH portion of the carboxylic acid group to be displaced in a nucleophillic substitution reaction is increased by reacting it with another species. In one embodiment of the invention the carboxylic acid moiety is reacted with an alcohol to form the corresponding ester which is more readily substituted by a nitrogen moiety.

Once the group of formula (1a) has been formed it is reacted with a nitrogen moiety typically a nitrogen of the formula:

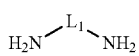

These reactions may be carried out in a number of ways although it is preferred if the amine can be used in excess to facilitate significant conversion of the starting material to the desired final product. The choice of nitrogen moiety to use will depend upon the desired $L_1$ group in the final product and the moiety will be chosen on this basis. An example of a particularly useful nitrogen moiety is 1,3-diamino propane.

The compound of formula (2) is then converted to a compound of formula (3) by reaction with a suitable reagent to introduce a moiety that is capable of binding with a biological entity. A wide number of reagents that are suitable for this purpose are known and the choice of reagent will depend upon the nature of the group you wish to introduce. Once the reagent is chosen this will determine the suitable reaction solvent and conditions in each individual case.

In some embodiments the compound of formula (2) is converted to a compound of formula (3) by reacting the amine with a reagent selected from the group consisting of an azide, thiophosgene, carbon disulphide and an acid anhydride. In some embodiments the reagent is an azide. In some embodiments the reagent is thiophosgene. In some embodiments the reagent is carbon disulphide. In some embodiments the reagent is maleic anhydride.

Examples of compounds of formula (3) that may be produced using the methodology described above include:

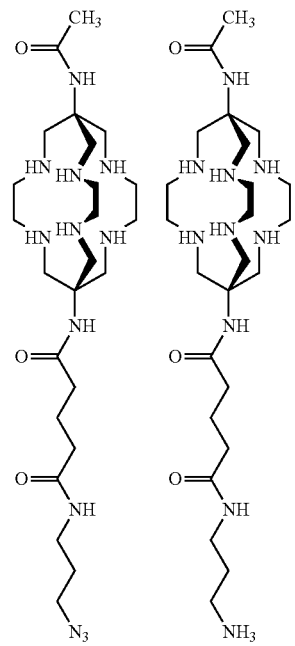

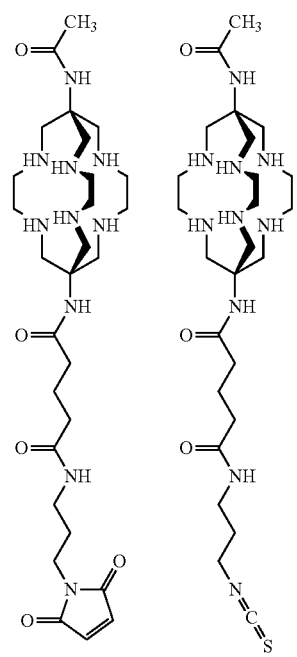

-continued

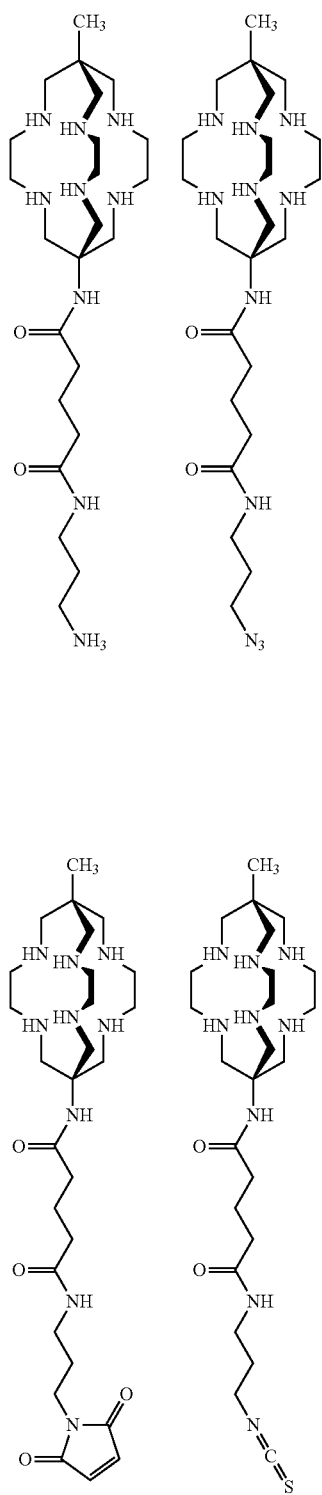

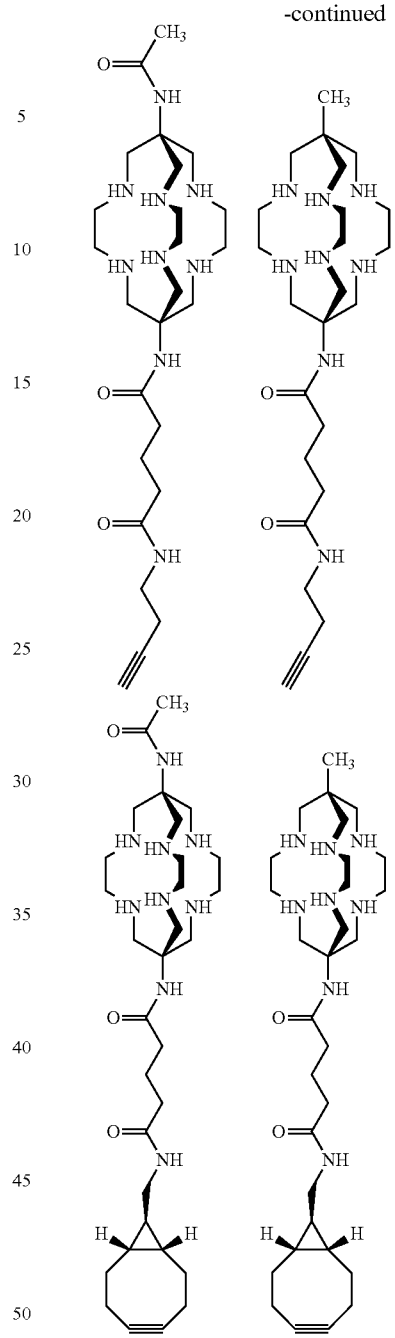

a metal complex thereof.

The formation of the metal complexes of the compounds synthesised in this way is carried out using techniques well known in the art.

These compounds may then be further elaborated to produce compounds of by reacting the reactive moiety with a suitable reactive element on a biological element. Thus for example where the R is a moiety capable of taking part in a click chemistry reaction with a complementary moiety on a biological entity the R group will be chosen depending upon the moieties on the biological entity of interest.

The formation of the metal complexes of the compounds synthesised in this way is carried out using techniques well known in the art.

As discussed above the compounds of the invention are useful as they can bind to a biological entity which can help them to be used in treatment of the human body. The compounds of formula (3) which have been attached to a biological entity and containing a radionuclide complexed with the ligand may be used in either radiotherapy or in diagnostic imaging applications. In each instance both therapy and diagnostic imaging will rely on the binding to the biological entity being involved in facilitating the localisation of the complex containing the radionuclide in the desired tissues or organs of the subject being treated/imaged.

Thus for example in relation to the use of the radiolabelled compounds of formula (3) it is anticipated that these will be used by first binding them to a biological entity of interest followed by administration of an effective amount of the radiolabelled compound to a subject followed by monitoring of the subject after a suitable time period to determine if the radiolabelled compound has localised at a particular location in the body or whether the compound is broadly speaking evenly distributed through the body. As a general rule where the radio labelled compound is localised in tissue or an organ of the body this is indicative of the presence in that tissue or organ of something that is recognised by the particular molecular recognition moiety used.

Accordingly judicious selection of a biological entity to connect the compound of formula (3) to is important in determining the efficacy of any of the radiolabelled compounds of the invention in diagnostic imaging applications. In this regard a wide range of biological entities that can act as molecular recognition moieties are known in the art which are well characterised and which are known to selectively target certain receptors in the body. In particular a number of biological entities that can act as molecular recognition moieties or molecular recognition portions are known that target tissue or organs when the patient is suffering from certain medical conditions. Examples of biological entities that can act as molecular recognition moieties or molecular recognition portions that are known and may be used in this invention include Octreotate, octreotide, [Tyr$^3$]-octreotate, [Tyr$^1$]-octreotate, bombesin, bombesin(7-14), gastrin releasing peptide, single amino acids, penetratin, annexin V, TAT, cyclic RGD, glucose, glucosamine (and extended carbohydrates), folic acid, neurotensin, neuropeptide Y, cholecystokinin (CCK) analogues, vasoactive intestinal peptide (VIP), substance P, alpha-melanocyte-stimulating hormone (MSH). For example, certain cancers are known to over express somatostatin receptors and so the molecular recognition moiety may be one which targets these receptors. An example of a molecular recognition moieties or molecular recognition portions of this type is [Tyr$^3$]-octreotate. Another example of a molecular recognition moieties or molecular recognition portions is cyclic RGD which is an integrin targeting cyclic peptide. In other examples a suitable molecular recognition moieties or molecular recognition portions is bombesin which is known to target breast and pancreatic cancers.

The monitoring of the subject for the location of the radiolabelled material will typically provide the analyst with information regarding the location of the radiolabelled material and hence the location of any material that is targeted by the molecular recognition moiety (such as cancerous tissue). An effective amount of the compounds of the invention will depend upon a number of factors and will of necessity involve a balance between the amount of radioactivity required to achieve the desired radio imaging effect and the general interest in not exposing the subject (or their tissues or organs) to any unnecessary levels of radiation which may be harmful.

The methods of treatment of the present invention involve administration of a compound of formula (3) which has been bound to a suitable biological entity and complexed to a radionuclide. The compounds of formula (3) after being bound to a biological entity are able to deliver the radionuclide to the desired location in the body where its mode of action is desired. As discussed above examples of suitable biological entities to act as molecular recognition moieties are known in the art and a skilled artisan can select the appropriate molecular recognition moiety to target the desired tissue in the body to be treated.

A therapeutically effective amount can be readily determined by an attending clinician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular radio labelled compound administered, the mode of administration, the bioavailability of the preparation administered, the dose regime selected, the use of other medications and other relevant circumstances.

In addition the treatment regime will typically involve a number of cycles of radiation treatment with the cycles being continued until such time as the condition has been ameliorated. Once again the optimal number of cycles and the spacing between each treatment cycle will depend upon a number of factors such as the severity of the condition being treated, the health (or lack thereof) of the subject being treated and their reaction to radiotherapy. In general the optimal dosage amount and the optimal treatment regime can be readily determined by a skilled addressee in the art using well known techniques.

In using the compounds of the invention they can be administered in any form or mode which makes the compound available for the desired application (imaging or radio therapy). One skilled in the art of preparing formulations of this type can readily select the proper form and mode of administration depending upon the particular characteristics of the compound selected, the condition to be treated, the stage of the condition to be treated and other relevant circumstances. We refer the reader to Remingtons Pharmaceutical Sciences, 19$^{th}$ edition, Mack Publishing Co. (1995) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found at least one container having a unit dosage of the agent(s). Conveniently, in the kits, single dosages can be provided in sterile vials so that the clinician can employ the vials directly, where the vials will have the desired amount and concentration of compound and radio nucleotide which may be admixed prior to use. Associated with such container(s) can be various written materials such as instructions for use, or a notice in the form prescribed by a governmental agency regulating the manufacture, use or sale of pharmaceuticals, imaging agents or biological products, which notice reflects approval by the agency of manufacture, use or sale for human administration.

The compounds of the invention may be used or administered in combination with one or more additional drug(s) that are anti-cancer drugs and/or procedures (e.g. surgery, radiotherapy) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs that include anti-cancer drugs, the compounds of the invention may be used in a combination therapy. When this is done the compounds are typically administered in combination with each other. Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

As discussed above, the compounds of the embodiments may be useful for treating and/or detecting proliferative diseases. Examples of such cell proliferative diseases or conditions include cancer (include any metastases), psoriasis, and smooth muscle cell proliferative disorders such as restenosis. The compounds of the present invention may be particularly useful for treating and/or detecting tumours such as breast cancer, colon cancer, lung cancer, ovarian cancer, prostate cancer, head and/or neck cancer, or renal, gastric, pancreatic cancer and brain cancer as well as hematologic malignancies such as lymphoma and leukaemia. In addition, the compounds of the present invention may be useful for treating and/or detecting a proliferative disease that is refractory to the treatment and/or detecting with other anti-cancer drugs; and for treating and/or detecting hyperproliferative conditions such as leukaemia's, psoriasis and restenosis. In other embodiments, compounds of this invention can be used to treat and/or detect pre-cancer conditions or hyperplasia including familial adenomatous polyposis, colonic adenomatous polyps, myeloid dysplasia, endometrial dysplasia, endometrial hyperplasia with atypia, cervical dysplasia, vaginal intraepithelial neoplasia, benign prostatic hyperplasia, papillomas of the larynx, actinic and solar keratosis, seborrheic keratosis and keratoacanthoma.

SYNTHESIS OF COMPOUNDS OF THE INVENTION

The agents of the various embodiments may be prepared using the reaction routes and synthesis schemes as described below, employing the techniques available in the art using starting materials that are readily available. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, $3^{rd}$ Edition, John Wiley & Sons, 1991. Alternatively, other reactions disclosed herein or known in the art will be recognized as having applicability for preparing other compounds of the various embodiments.

Reagents useful for synthesizing compounds may be obtained or prepared according to techniques known in the art.

Synthetic procedures for the synthesis of selected compounds of formula (1) are detailed below.

EXAMPLES

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeal bottles and used as received. All solvents were purified by using standard methods in the art, unless otherwise indicated. SP Sephadex C25 and DOWEX 50w×2 200-400 mesh cation exchange resin was purchased from Aldrich. Fmoc-L-amino acids, HATU, HCTU and 2-chlorotrityl resin were purchased from GL Biochem Ltd (Shanghai, China). Fmoc-Lys(iv-Dde)-OH and Fmoc-D-amino acids were purchased from Bachem AG (Switzerland). Fmoc-Pal-PEG-PS resin was purchased from Applied Biosystems (Foster City, Calif.). Nova PEG Rink Amide resin was purchased from NovaBiochem, Darmstadt, Germany. $[Co((NO_2)_2sar)]Cl_3$, $[Co((NH_2)_2sar)]Cl_3$, $(NH_2)_2$sar, $[Cu(NH_3)_2sar](CF_3SO_3)_4$ were prepared according to established procedures. (1) Geue, R. J.; Hambley, T. W.; Harrowfield, J. M.; Sargeson, A. M.; Snow, M. R. *J. Am. Chem. Soc.* 1984, 106, 5478-5488. (2) Bottomley, G. A.; Clark, I. J.; Creaser, I. I.; Engelhardt, L. M.; Geue, R. J.; Hagen, K. S.; Harrowfield, J. M.; Lawrance, G. A.; Lay, P. A.; Sargeson, A. M.; See, A. J.; Skelton, B. W.; White, A. H.; Wilner, F. R. *Aust. J. Chem.* 1994, 47, 143-179 and (3) Bernhardt, P. V.; Bramley, R.; Engelhardt, L. M.; Harrowfield, J. M.; Hockless, D. C. R.; Korybut-Daszkiewicz, B. R.; Krausz, E. R.; Morgan, T.; Sargeson, A. M.; Skelton, B. W.; White, A. H. *Inorg. Chem.* 1995, 34, 3589-3599.

The reactions set forth below were performed under a positive pressure of nitrogen, argon or with a drying tube, at ambient temperature (unless otherwise stated), in anhydrous solvents, and the reaction flasks are fitted with rubber septa for the introduction of substrates and reagents via syringe. Glassware was oven-dried and/or heat-dried.

Work-ups were typically done by doubling the reaction volume with the reaction solvent or extraction solvent and then washing with the indicated aqueous solutions using 25% by volume of the extraction volume (unless otherwise indicated). Product solutions were dried over anhydrous sodium sulfate prior to filtration, and evaporation of the solvents was under reduced pressure on a rotary evaporator and noted as solvents removed in vacuo. Flash column chromatography [Still et al, J. Org. Chem., 43, 2923 (1978)] was conducted using E Merck-grade flash silica gel (47-61 mm) and a silica gel:crude material ratio of about 20:1 to 50:1, unless otherwise stated. Hydrogenolysis was done at the pressure indicated or at ambient pressure.

Mass spectra were recorded in the positive ion mode on an Agilent 6510 Q-TOF LC/MS Mass Spectrometer coupled to an Agilent 1100 LC system (Agilent, Palo Alto, Calif.). Data were acquired and reference mass corrected via a dual-spray electrospray ionisation source, using the factory-defined calibration procedure. Each scan or data point on the Total Ion Chromatogram is an average of 9652 transients, producing 1.02 scans $s^{-1}$. Spectra were created by averaging the scans across each peak. Mass spectrometer conditions: fragmentor: 200-300 V; drying gas flow: 7 L/min; nebuliser: 30 psi; drying gas temp: 325° C.; $V_{cap}$: 4000 V; skimmer: 65 V; OCT R$_f$V: 750 V; scan range acquired: 150-3000 m/z.

HPLC-MS traces were recorded using an Agilent Eclipse Plus C18 column (5 μm, 2.1×150 mm) coupled to the Agilent 6510 Q-TOF LC/MS Mass Spectrometer described above. 1 μL aliquots of each sample were injected onto the column using the Agilent 1100 LC system, with a flow rate of 0.5 mL/min. Data acquisition parameters are the same as those described above for mass spectra, with the exception of the fragmentor (fragmentor voltage: 100 V).

NMR spectra were recorded on a Varian FT-NMR 500 spectrometer operating at 500 MHz for $^1$H NMR and 125.7 MHz for $^{13}$C-NMR. NMR spectra are obtained as $D_2O$ solutions (reported in ppm), using acetone as the reference standard (2.22 ppm and 30.89 ppm respectively). Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Semi-preparative HPLC purifications were performed using an Agilent 1200 Series HPLC system with a 5 mL/min flow rate. Solvent gradients and column specifications are described in the examples. An automated Agilent 1200 fraction collector collected 1-3 mL fractions and fraction collection was based on UV-Vis detection at 214 or 220 nm, with a lower threshold limit between 100-400 mAU. Each fraction was analysed using MS and analytical HPLC.

Analytical HPLC traces were acquired using an Agilent 1200 Series HPLC system and an Agilent Zorbax Eclipse XDB-C18 column (4.6×150 mm, 5 μm) with a 1 mL/min flow rate and UV spectroscopic detection at 214 nm, 220 nm and 270 nm.

UV-Vis spectra were acquired on a Cary 300 Bio UV-Vis spectrophotometer, from 800-200 nm at 0.500 nm data intervals with a 300.00 nm/min scan rate.

Voltametric experiments were performed with an Autolab (Eco Chemie, Utrecht, Netherlands) computer-controlled electrochemical workstation. A standard three-electrode arrangement was used with a glassy carbon disk (d, 3 mm) as working electrode, a Pt wire as auxiliary electrode and a Ag/AgCl reference electrode (silver wire in $H_2O$ (KCl (0.1 M) $AgNO_3$ (0.01 M)). Scan rate: 100 mV/s, sample interval: 1.06 mV, sensitivity: $1 \times 10^{-4}$ A.

HPLC traces of radiolabelled peptides were acquired using a Waters Comosil C18 column (4.6×150 mm) coupled to a Shimadzu LC-20AT with a sodium iodide scintillation detector and a UV-Vis detector. 100 μL aliquots of each radiolabelled sample were injected onto the column, using a flow rate of 1 mL/min.

The following examples are intended to illustrate the embodiments disclosed and are not to be construed as being limitations thereto. Additional compounds, other than those described below, may be prepared using the following described reaction scheme or appropriate variations or modifications thereof.

Example 1

$CuL^2Cl_2.xHCl$

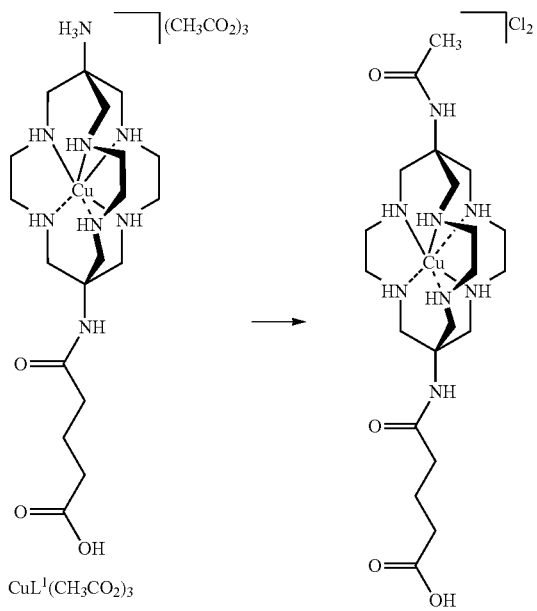

$CuL^1(CH_3CO_2)_3.xH_2O$ (644 mg) was dissolved in acetic anhydride (10 mL) and the resulting blue solution taken to dryness by rotary evaporation (60° C.). The residue was redissolved in $H_2O$ and applied to a column of Dowex 50W×2 (10 cm height, 3 cm diameter). After washing with water (100 mL) and 1M HCl (100 mL) the complexes were eluted with 3M HCl. The first major band was collected and the solvent removed by rotary evaporation to yield the chloride salt as a purple solid (798 mg). MS: $[CuC_{21}H_{42}N_8O_4]^{2+}$ m/z=266.63 (experimental), 266.63 (calculated).

Example 2

$L^2.xHCl$

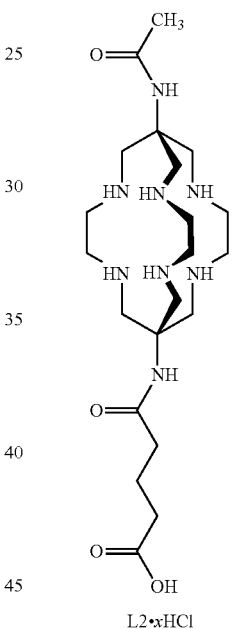

A solution of $CuL^2Cl_2.xHCl$ in water in a two-neck flask was deoxygenated by purging with $N_2$ gas for 20 mins. Under an atmosphere of $N_2$ gas, sodium sulfide was added and the solution turned dark green with a black precipitate. The reaction was stirred overnight at room temperature. After ~20 hours, suspension was filtered (Whatman Filter Paper 1) and the filtrate diluted with 1 M HCl (200 mL) resulting in the formation of a cloudy, white precipitate. This precipitate was allowed to settle for 2 h before it was filtered through a Millipore Steritop™ (0.22 μm, 500 mL) filter and applied to a DOWEX 50W×2 cation exchange column ($H^+$ form, 10×3 cm). The column was washed with 1 M HCl solution (500 mL) (to remove $Na_2S$) and then slowly eluted with 4 M HCl solution (200 mL). The eluent was evaporated to dryness under reduced pressure to give a white solid.

Example 3

CuL³(CH₃CO₂)₂

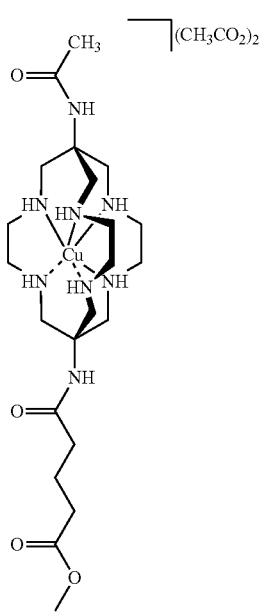

CuL3(CH3CO2)2

CuL²Cl₂.xH₂O (434 mg) was dissolved in methanol (20 mL) and the solvent was removed by rotary evaporation (50° C.). The residue was converted to the acetate salt by anion exchange chromatography on the acetate form of Dowex 1×8. The slurry was filtered and the solvent removed by rotary evaporation and taken to dryness. The blue residue was dissolved in methanol before the solvent was removed by rotary evaporation and taken to dryness to give a blue residue (366 mg). MS: $[CuC_{22}H_{44}N_8O_4]^{2+}$ m/z=273.66 (experimental), 273.64 (calculated).

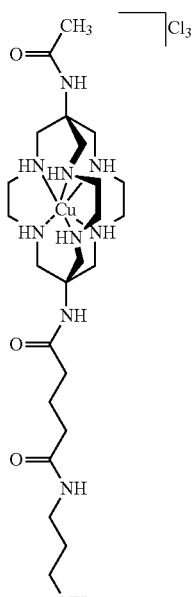

CuL4Cl3

Example 4

CuL⁴Cl₃

CuL³(CH₃CO₂)₂ (360 mg) was dissolved in 1,3-diaminopropane (5 mL) and the solution was stirred at room temperature for 40 h. The solution was diluted with water and applied to a column of SP-Sephadex C-25 (30 cm height, 3 cm diameter). After washing with water (100 mL), the complexes were eluted with 0.3 M NaCl to yield a minor leading band of hydrolysed ester and a major band of the amine product. The blue solution was applied to a column of Dowex 50W×2 (10 cm height, 3 cm diameter). After washing with water (100 mL) and 1M HCl (100 mL) the complex was eluted with 3M HCl. The solvent was removed by rotary evaporation and taken to dryness (422 mg). MS: $[CuC_{24}H_{50}N_{10}O_3]^{2+}$ m/z=294.67 (experimental), 294.67 (calculated).

Example 5

L⁴.xCH₃CO₂H

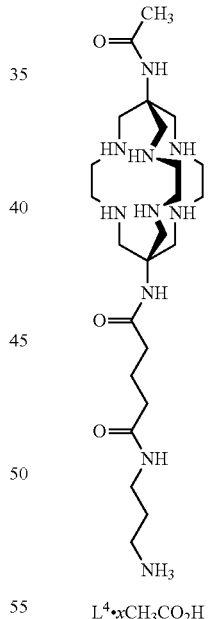

L⁴·xCH₃CO₂H

A solution of CuL⁴Cl₃.xHCl (511 mg) in water (4 mL) in a two-neck flask was deoxygenated by purging with N₂ gas for 20 mins. Under an atmosphere of N₂ gas, sodium sulfide (766 mg) was added and the solution turned dark green with a black precipitate. The reaction was stirred overnight at room temperature. After ~20 hours, suspension was filtered (Whatman Filter Paper 1) and the filtrate diluted with 1 M HCl (200 mL) resulting in the formation of a cloudy, white precipitate. This precipitate was allowed to settle for 2 h before it was filtered through a Millipore Steritop™ (0.22 μm, 500 mL) filter and applied to a DOWEX 50W×2 cation exchange column (H+ form, 10×3 cm). The column was washed with 1 M HCl solution (500 mL) (to remove Na$_2$S) and then slowly eluted with 4 M HCl solution (200 mL). The eluent was evaporated to dryness under reduced pressure to give a white solid (413 mg). The residue was converted to the acetate salt by anion exchange chromatography on the acetate form of Dowex 1×8. The slurry was filtered and the solvent removed by rotary evaporation and taken to dryness. The colourless residue was dissolved in methanol before the solvent was removed by rotary evaporation and taken to dryness to give a colourless residue (396 mg). MS: $[C_{24}H_{51}N_{10}O_3]^+$ m/z=527.42 (experimental), 527.41 (calculated).

Example 6

$L^5$·xHCl

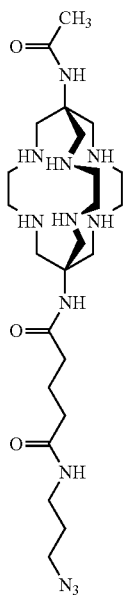

$L^5$·xHCl

To a mixture of sodium azide in water and dichloromethane was added triflic anhydride at 0° C. The mixture was allowed to warm to room temperature and was stirred vigorously for 2.5 h. The aqueous layer was removed and washed with dichloromethane. The organic layers were combined and added dropwise to a solution of $L^4$·xCH$_3$CO$_2$H, K$_2$CO$_3$ and Zn(CH$_3$CO$_2$)$_2$·2H$_2$O in methanol and water. The mixture was stirred vigorously for 3 h. The organic layer was removed and the aqueous layer applied to a column of Dowex 50W×2 (10 cm height, 3 cm diameter). After washing with water (100 mL) and 1M HCl (100 mL) to remove Zn$^{2+}$, the protonated ligand was eluted with 3M HCl. The solvent was removed by rotary evaporation to yield the chloride salt.

Example 7

$L^6$·xCH$_3$CO$_2$H

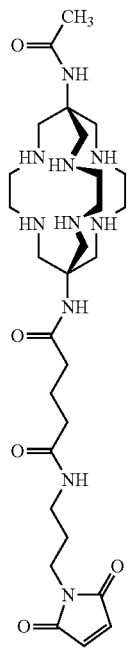

To a solution of $L^4$·xCH$_3$CO$_2$H in acetic acid was added maleic anhydride and the reaction was heated at 60° C. in a water bath for 30 min before the solvent was removed by rotary evaporation (60° C.). Residual acetic acid was removed by azeotroping with toluene and then taken to dryness.

Example 8

$L^7$·xCH$_3$CO$_2$H

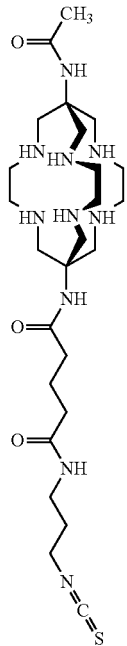

To a solution of thiophosgene in chloroform was added a solution of $L^4$·xCH$_3$CO$_2$H in water and the mixture was stirred vigorously for 12 h. The aqueous layer removed, washed with chloroform and taken to dryness.

Example 9

CuL⁸Cl₂.xHCl

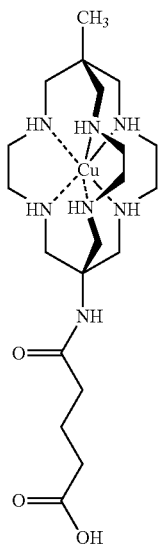

To a solution of [Cu(CH₃)(NH₃)sar](CF₃SO₃)₃ (0.3 g, 0.1 mmol) in anhydrous N,N-dimethylacetamide (DMA) (5 mL) was added glutaric anhydride (0.08 g, 1. mmol) and diisopropylethylamine (132 μL) were added and the solution was heated at 70° C. for 5 h. The reaction was monitored using a microcolumn of SP Sephadex C-25 cation exchange (Na⁺ form) eluting with 0.05 M sodium citrate solution. The solution was cooled and water (20 mL) was added. The solution was applied to a column of SP Sephadex C-25 cation exchange (Na⁺ form, 6×3 cm). After washing with water, the complexes were eluted with 0.05 M sodium citrate solution to yield the major leading band as the carboxylate product and a minor band of unreacted copper complex. The major band was applied to a Dowex 50W×2 cation exchange column (H⁺ form, 10×5 cm). After the column was washed with water (500 mL) and 1 M HCl solution (500 mL) and the complex was eluted with 3 M HCl and the eluent was evaporated to dryness under reduced pressure at 40° C. giving a purple residue (0.23 g).

Example 10

L⁸.xHCl

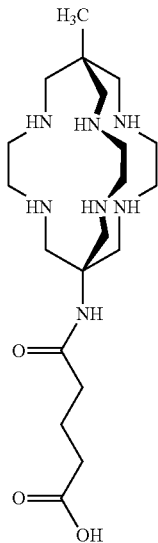

A solution of CuL⁸Cl₂.xHCl (0.1 g) in water (5 mL) in a two-neck flask was deoxygenated by purging with N₂ gas for 20 mins. Under an atmosphere of N₂ gas, sodium sulfide (0.14 g) was added and the solution turned dark green with a black precipitate. The reaction was stirred overnight at room temperature. After ~20 hours, suspension was filtered (Whatman Filter Paper 1) and the filtrate diluted with 1 M HCl (150 mL) resulting in the formation of a cloudy, white precipitate. This precipitate was allowed to settle for 2 h before it was filtered through a Millipore Steritop™ (0.22 μm, 500 mL) filter and applied to a Dowex 50W×2 cation exchange column (H⁺ form, 10×3 cm). The column was washed with 1 M HCl solution (150 mL) (to remove Na₂S) and then slowly eluted with 4 M HCl solution (300 mL). The eluent was evaporated to dryness under reduced pressure to give a white solid (0.09 g). MS: $[C_{20}H_{42}N_7O_3]^+$ m/z=428.34 (experimental), 428.33 (calculated). ¹H NMR (D₂O): δ=1.03, s, CH₃; 1.91, m, 2H, 2.35, t, ³J=7.5, 2H, CH₂; 2.45, t, ³J=7, 2H, CH₂; 3.1-3.5, broad, 24H, cage CH₂. ¹³C NMR (D₂O, residual acetone 30.9, 215.9): δ=19.4, CH₃; 21.0, 33.4, 35.4, glutarate CH₂; 37.1 46.3, 48.4, 51.8, 54.2, 57.4, cage CH₂); 177.8, 178.5, CO.

Example 11

CuL⁹(CH₃CO₂)₂

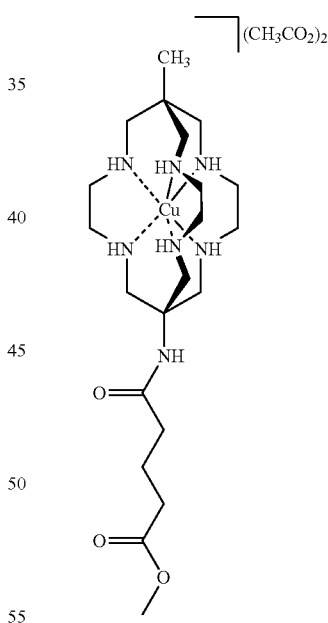

CuL⁸Cl₂.xH₂O (0.2 g) was dissolved in methanol (3 mL) and the solvent was removed by rotary evaporation (40° C.). The residue was converted to the acetate salt by anion exchange chromatography on the acetate form of Dowex 1×8. The slurry was filtered and the solvent removed by rotary evaporation and taken to dryness. The blue residue was dissolved in methanol before the solvent was removed by rotary evaporation and taken to dryness to give a blue residue (0.2 g). MS: $[CuC_{21}H_{43}N_7O_3]^{2+}$ m/z=(experimental), 252.14 (calculated).

Example 12
CuL¹⁰Cl₃

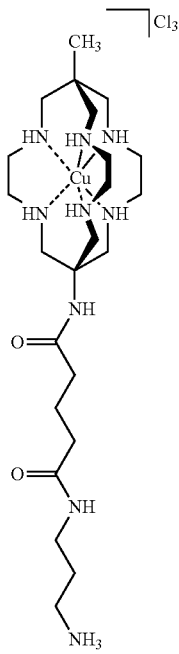

CuL⁹(CH₃CO₂)₂ was dissolved in 1,3-diaminopropane and the solution was stirred at room temperature for 40 h. The solution was diluted with water and applied to a column of SP-Sephadex C-25 (30 cm height, 3 cm diameter). After washing with water (100 mL), the complexes were eluted with 0.3 M NaCl to yield a minor leading band of hydrolysed ester and a major band of the amine product. The blue solution was applied to a column of Dowex 50W×2 (10 cm height, 3 cm diameter). After washing with water (100 mL) and 1M HCl (100 mL) the complex was eluted with 3M HCl. The solvent was removed by rotary evaporation and taken to dryness.

Example 13
L¹⁰.xCH₃CO₂H

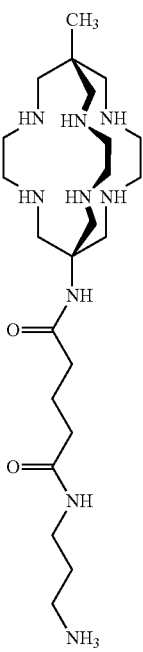

A solution of CuL¹⁰Cl₃.xHCl in water in a two-neck flask was deoxygenated by purging with N₂ gas for 20 mins. Under an atmosphere of N₂ gas, sodium sulfide was added and the solution turned dark green with a black precipitate. The reaction was stirred overnight at room temperature. After ~20 hours, suspension was filtered (Whatman Filter Paper 1) and the filtrate diluted with 1 M HCl (200 mL) resulting in the formation of a cloudy, white precipitate. This precipitate was allowed to settle for 2 h before it was filtered through a Millipore Steritop™ (0.22 µm, 500 mL) filter and applied to a DOWEX 50W×2 cation exchange column (H⁺ form, 10×3 cm). The column was washed with 1 M HCl solution (500 mL) (to remove Na₂S) and then slowly eluted with 4 M HCl solution (200 mL). The eluent was evaporated to dryness under reduced pressure to give a white solid. The residue was converted to the acetate salt by anion exchange chromatography on the acetate form of Dowex 1×8. The slurry was filtered and the solvent removed by rotary evaporation and taken to dryness. The colourless residue was dissolved in methanol before the solvent was removed by rotary evaporation and taken to dryness to give a colourless residue.

Example 14
L¹¹.xHCl

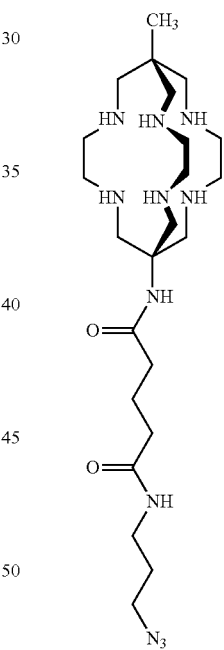

To a mixture of sodium azide in water and dichloromethane was added triflic anhydride at 0° C. The mixture was allowed to warm to room temperature and was stirred vigorously for 2.5 h. The aqueous layer was removed and washed with dichloromethane. The organic layers were combined and added dropwise to a solution of L¹⁰.xCH₃CO₂H, K₂CO₃ and Zn(CH₃CO₂)₂.2H₂O in methanol and water. The mixture was stirred vigorously for 3 h. The organic layer was removed and the aqueous layer applied to a column of Dowex 50W×2 (10 cm height, 3 cm diameter). After washing with water (100 mL) and 1M HCl (100 mL) to remove Zn²⁺, the protonated ligand was eluted with 3M HCl. The solvent was removed by rotary evaporation to yield the chloride salt.

Example 15

$L^{12} \cdot xCH_3CO_2H$

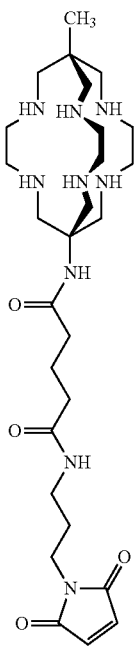

To a solution of $L^{10} \cdot xCH_3CO_2H$ in acetic acid was added maleic anhydride and the reaction was heated at 60° C. in a water bath for 30 min before the solvent was removed by rotary evaporation (60° C.). Residual acetic acid was removed by azeotroping with toluene and then taken to dryness.

Example 16

$L^{13} \cdot xCH_3CO_2H$

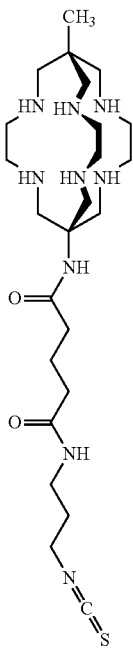

To a solution of thiophosgene in chloroform was added a solution of $L^4 \cdot xCH_3CO_2H$ in water and the mixture was stirred vigorously for 12 h. The aqueous layer removed, washed with chloroform and taken to dryness.

Finally, it will be appreciated that various modifications and variations of the methods and compositions of the invention described herein will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are apparent to those skilled in the art are intended to be within the scope of the present invention.

What is claimed is:
1. A method of functionalizing a compound of the formula (1) or a metal complex thereof:

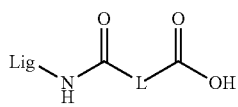

Formula (1)

wherein Lig is a nitrogen containing macrocyclic metal ligand of the formula

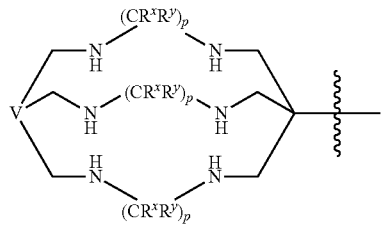

V is selected from the group consisting of N and $CR^1$;
each $R^x$ and $R^y$ are independently selected from group consisting of H, $CH_3$, and $CO_2H$, $NO_2$, $CH_2OH$, $H_2PO_4$, $HSO_3$, CN, $CONH_2$ and CHO;
each p is independently an integer selected from the group consisting of 2, 3, and 4;
$R^1$ is selected from the group consisting of H, OH, halogen, $NO_2$, $NH_2$, optionally substituted $C_1$-$C_{12}$alkyl, optionally substituted $C_6$-$C_{18}$aryl, cyano, $CO_2R^2$, $NHR^3$ and $N(R^3)_2$;
$R^2$ is selected from the group consisting of H, halogen, an oxygen protecting group, substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl; and
each $R^3$ is independently selected from the group consisting of H, a nitrogen protecting group, optionally substituted $C_1$-$C_{12}$alkyl, —(C=O)-substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;
L is a group of the formula

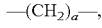

$—(CH_2)_a—$, wherein optionally one or more of the $CH_2$ groups may be independently replaced by a heteroatomic group selected from S, O and $NR^4$ where $R^4$ is selected from the group consisting of H, optionally substituted $C_1$-$C_{12}$alkyl optionally substituted $C_3$-$C_{12}$cycloalkyl optionally substituted $C_6$-$C_{18}$aryl, and optionally substituted $C_1$-$C_{18}$heteroaryl;

a is an integer selected from the group consisting of 1, 2, 3, 4, 5, 6, 7, 8, 9 and 10;

the method comprising;

(a) converting the compound of formula (1) or a metal complex thereof to a compound of formula (II) or a metal complex thereof

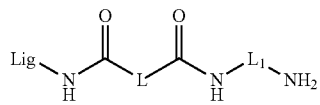

Formula (2)

wherein $L^1$ is a spacer group of the formula

$-(CH_2)_a-$, wherein optionally one or more of the CH$_2$ groups may be independently replaced by a heteroatomic group selected from S, O and NR$^4$ where R$^4$ is selected from the group consisting of H, optionally substituted C$_1$-C$_{12}$alkyl, optionally substituted C$_3$-C$_{12}$cycloalkyl, optionally substituted C$_6$-C$_{18}$aryl, and optionally substituted C$_1$-C$_{18}$heteroaryl;

a is an integer selected from the group consisting of 1, 2, 3, 4, 5, 6, 7, 8, 9 and 10;

(b) converting the compound of formula (2) or a metal complex thereof to a compound of formula (3) or a metal complex thereof

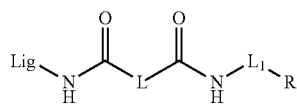

Formula (3)

wherein R or a protected form thereof is a moiety capable of binding to a molecular recognition moiety.

2. The method according to claim 1 wherein step (a) comprises the steps of:

(a1) converting the compound of formula (1) into a compound of formula (Ia)

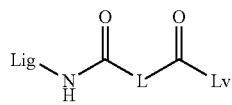

wherein Lv is a leaving group that can be displaced by a nitrogen moiety in a nucleophilic substitution reaction;

(a2) reacting the compound of formula (1a) with a nitrogen nucleophile of the formula:

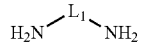

to form a compound of formula (2).

3. The method according to claim 1 wherein the compound of formula (2) is converted to a compound of formula (3) by reacting the amine with a reagent selected from the group consisting of an azide, thiosphosgene, carbon disulphide and an acid anhydride.

4. The method according to claim 3 wherein the reagent is an azide.

5. The method according to claim 3 wherein the reagent is thiosphosgene.

6. The method according to claim 3 wherein the reagent is maleic anhydride.

7. The method according to claim 1, wherein Lig is selected from the group consisting of:

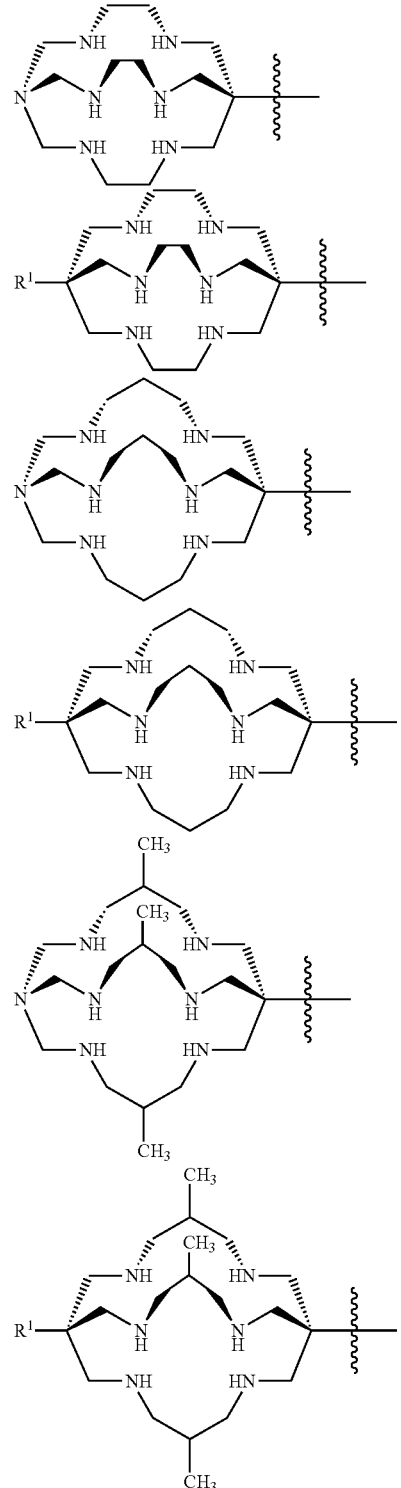

and wherein R$^1$ is as defined in claim 1.

8. The method according to claim 1 wherein a is an integer selected from the group consisting of 1, 2, 3, 4, and 5.

9. The method according to claim 1 wherein L is selected from the group consisting of $-CH_2-$, $-CH_2CH_2-$, $-CH_2CH_2CH_2-$, $-CH_2CH_2CH_2CH_2-$ and $-CH_2OCH_2-$.

10. The method according to claim 1, wherein L is $-CH_2CH_2CH_2-$.

11. The method according to claim 1 wherein a is an integer selected from the group consisting of 1, 2, 3, 4, and 5.

12. The method according to claim 1 wherein $L^1$ is selected from the group consisting of $-CH_2-$, $-CH_2CH_2-$, $-CH_2CH_2CH_2-$, and $-CH_2CH_2CH_2CH_2-$.

13. The method according to claim 1, wherein $L^1$ is $-CH_2CH_2CH_2$.

14. The method according to claim 1 wherein R is a moiety capable of taking part in a click chemistry reaction with a complementary moiety on a molecular recognition moiety, wherein R is selected from the group consisting of $-NCS$, $CO_2H$, $NH_2$, an azide, an alkyne, an isonitrile, and a tetrazine, or a protected form thereof.

15. The method according to claim 1, wherein the compound is in the form of a metal complex when subjected to conversion or reaction.

16. The method according to claim 15, wherein the metal is magnesium.

* * * * *